(12) United States Patent
Xu et al.

(10) Patent No.: US 7,704,976 B2
(45) Date of Patent: *Apr. 27, 2010

(54) USE OF N-ACETYL-D-GLUCOSAMINE FOR PREPARING MEDICINES FOR UROGENITAL TRACT INFECTION'S TREATMENT AND PREVENTION

(75) Inventors: Qiwang Xu, Chongqing (CN); Junkang Liu, Chongqing (CN); Zetao Yuan, Chongqing (CN)

(73) Assignees: Third Military Medical University, Chinese People's Liberation Army, P.R. of China (CN); Bio-Wave Institute of Suzhou Hi-Tech New District Corporation, Ltd. (CN); Beijing Sino-HongKong Dafu Science & Technology of Biowave, Ltd. (CN)

( * ) Notice: Subject to any disclaimer, the term of this patent is extended or adjusted under 35 U.S.C. 154(b) by 1099 days.

This patent is subject to a terminal disclaimer.

(21) Appl. No.: 10/524,476

(22) PCT Filed: Aug. 13, 2003

(86) PCT No.: PCT/CN03/00664

§ 371 (c)(1),
(2), (4) Date: Oct. 11, 2005

(87) PCT Pub. No.: WO2004/014398

PCT Pub. Date: Feb. 19, 2004

(65) Prior Publication Data

US 2006/0142243 A1  Jun. 29, 2006

(30) Foreign Application Priority Data

Aug. 13, 2002  (CN) ............................... 02 1 25486

(51) Int. Cl.
*A01N 43/04* (2006.01)
*A61K 31/70* (2006.01)

(52) U.S. Cl. ...................................................... 514/62

(58) Field of Classification Search ....................... None
See application file for complete search history.

(56) References Cited

U.S. PATENT DOCUMENTS

| 5,116,615 | A | 5/1992 | Gokeen et al. |
| 5,229,374 | A | 7/1993 | Burton et al. |
| 6,037,333 | A * | 3/2000 | Panjwani ..................... 514/62 |
| 6,046,179 | A | 4/2000 | Murch et al. |
| 7,238,677 | B2 * | 7/2007 | Yang et al. ................... 514/54 |
| 2003/0149090 | A1 * | 8/2003 | Gehlsen et al. ............. 514/400 |
| 2004/0092483 | A1 | 5/2004 | Xu et al. |

FOREIGN PATENT DOCUMENTS

| JP | 2002020293 | 1/2002 |
| WO | 9706810 | 2/1997 |

OTHER PUBLICATIONS

Strohmaier, W.L. et al., "Therapie der Interstitiellen BZW Radiogenen Zystitis Mit D-Glukasamin," Helvetica Chirurgica Acta, Schwabe & Co., Basel, vol. 56, No. 3, Aug. 1989, pp. 323-325.
Bhavanadan VP, "Glycosaminoglycans and glycoproteins of animal bladder," Connective Tissue 2001 Japan, vol. 33, No. 3, 2001, pp. 245-252.

* cited by examiner

*Primary Examiner*—Traviss C McIntosh, III
(74) *Attorney, Agent, or Firm*—Price, Heneveld, Cooper, DeWitt & Litton, LLP

(57) ABSTRACT

The present invention discloses a use of N-acetyl-D-glucosamine in the manufacture of a medicament for treatment of urogenital tract infection. N-acetyl-D-glucosamine exhibits a function of suppressing the transplantation of exotic microorganisms and promoting the repair of topical skin tissue, and the formulation comprising it as a main active component is used for the prevention and treatment of urogenital tract infection and has advantages such as notable therapeutic effect, easy preparation, non-irritation, non-contamination, etc.

18 Claims, No Drawings

USE OF N-ACETYL-D-GLUCOSAMINE FOR PREPARING MEDICINES FOR UROGENITAL TRACT INFECTION'S TREATMENT AND PREVENTION

TECHNICAL FIELD

The present invention relates to the use of N-acetyl-D-glucosamine in the manufacture of a medicament for treating urogenital tract infection.

BACKGROUND ART

Urogenital tract infection is a common disease, which is chronic and refractory and greatly interferes with a patient's normal life. At present, the main medicaments for treating urogenital tract infection mainly are broad spectrum antibiotics and Chinese lotion. However, the abuse of broad spectrum antibiotics results in drug resistance in microorganisms causing urogenital tract infection, so that the therapeutic effect became worse and worse although the dose of antibiotics increased gradually. On the other hand, the conventional treatment with antibiotics can hardly bring about better effect. For example, condyloma acuminatum virus can hardly be treated. In addition, the treatment of urogenital tract infection with Chinese lotion also has disadvantages, for example, unremarkable effect, inconvenient use, and contamination of clothing. Hence, a medicament for effectively treating urogenital tract infection is in need.

In the research of "bio-waves" theory, the present inventor has set up a bacterial wave growth model. Through researching, it is known that this wave is of its intrinsic regulation mechanism: some chemical substances are able to participate the regulation in the bio-wave process, so as to transform an abnormal periodic slow wave into a normal physiological chaotic quick wave, and these kind of substances are known as promoting wave factors. Through separating, purifying and identifying, it is determined that one of the factors is N-acetyl-D-glucosamine, the promoting wave function of which is shown in regulating the coupling oscillation of cellular membrane protein and sugar coating. Many biochemical and physiological processes of the human body need the participation of the promoting wave factors, and it would lead to an abnormal state, if these kind of promoting wave factors are lacking in the living body.

N-acetyl-D-glucosamine is a chemical reagent. From the 1990s, it has been continually used to treat diseases such as pericementittis (WO9102530A1), intestinal inflammation (WO9953929A 1), cornea disease (JP10287570A2), hypertrophy of the prostate (US05116615), organic pathologic changes of lower digestive tract mucous membrane (WO93/1475), etc. as a tissue growth regulation agent (WO18702244), and in cosmetology (JP59013708A2), shampoo preparation (JP2011505A2), etc., but it has not been used in the manufacture of a medicament for treating urogenital tract infection.

CONTENTS OF THE INVENTION

The present invention surprisingly discovers that N-acetyl-D-glucosamine can be used to effectively treat urogenital tract infection. This discovery is surprising because the heal of urogenital tract infection needs to control microorganism infection, to treat topical exudation, to eliminate tissue inflammatory edema and pains, to promote tissue repair, and so on, and a doctor usually provides a combination of several medicaments, while N-acetyl-D-glucosamine could be used as the only active ingredient in a medicament for healing urogenital tract infection.

Based on the above discovery, the present application relates to the use of N-acetyl-D-glucosamine and pharmaceutical acceptable salt thereof in the manufacture of a medicament for treating urogenital tract infection.

On the other hand, the present invention relates to a method for treating urogenital tract infection, comprising administrating to a patient in need of this treatment an effective amount of N-acetyl-D-glucosamine or a pharmaceutical acceptable salt thereof.

N-acetyl-D-glucosamine is a compound of the following formula.

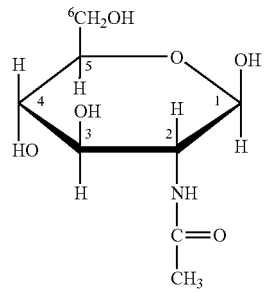

N-acetyl-D-glucosamine is commercially available from the market or prepared according to a known method. For instance, WO97/31121 discloses a method for preparing N-acetyl-D-glucosamine from chitin by an enzyme method. JP63273493 discloses a method comprising partially hydrolyzing chitin to obtain N-acetyl-chitose, and then treating it with an enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids such as hydrochloride, hydrobromide, borate, phosphate, sulfate, hydrosulfate and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate, α-glyceryl phosphate and glucose-1-phosphate.

The compound of the formula (I) or its pharmaceutically acceptable salt is used as a main active component in combination with several pharmaceutically acceptable excipients and/or carriers to prepare a topical formulation form such as aqua, emulsion, cream, lotion, ointment, suppository, etc. for treatment of urogenital tract infection. The amount of the active component is 0.1 to 10%, preferably 0.2 to 6% relative to the whole formulation. The daily dose of said medicament is 10 to 10000 mg, preferably 50 to 5000 mg, more preferably 100 to 2000 mg of N-acetyl-D-glucosamine per person.

The composition of the present invention in the form of topical formulation, such as solution, emulsion, suspension, viscoloid, cream, ointment, etc. for topically daubing or washing, can be prepared by mixing the active component with one or more pharmaceutically acceptable carriers and additives, such as water, polyethylene glycol, glycerin, Vaseline, xanthan gum, alcohols, etc. as a dissolving agent, lubricant, binder, preservative, stabilizer, and in combination with an ecological regulator such as lactic acid according to general techniques as well known by the person skilled in the art. In addition, a propellant can be added to said formulation to prepare an aerosol for topically spraying. For example, an aerosol has a formulation comprising 1% N-acetyl-D-glucosamine, 3% lactic acid and 0.3% sodium benzoate.

Unrestricted to any theory, the inventor deems the effect of the compound of formula (I) of the present invention for treatment of urogenital tract infection is achieved by adjusting the redistribution of body cells. "Cell redistribution" means the continued position alternation of body tissue cells of microorganism cells and the rhythmic alternation of coagulation-dissolution state of biological macromolecules in cells. N-acetyl-D-glucosamine brings about a special function by regulating cell redistribution in different levels. The alternation of macroscopic cell position represents the feature of the cell growth in a wave manner. N-acetyl-D-glucosamine regulates the growth of body cells and microorganism cells in a normal wave manner, so that microorganisms cannot be topically transplanted. As for microecological function, the normal bacteria growth is supported, and the supplement of ecological bacteria is not employed, so that the disadvantage of adaptability of the supplementary bacteria is avoided. In terms of promoting repair of skin and mucous membrane tissues, the product of the present invention exhibits unique effects for controlling inflammation, damage, infection, and exudation. Thus, the product of the present invention can be widely used for controlling conditions and for essential treatment.

The following experimental examples are used to illustrate the promoting wave function, low toxicity, activity for suppressing microorganism transplantation, and clinical effect for treatment of urogenital tract infection.

1. Promoting Wave Test of the Compound of Formula (I)

1. Experimental Materials and Method:

1.1 Samples: Pure Compound of Formula (I)

1.2 Experimental Materials:
  Strain: *Proteus Mirabilis* and *lactobacillus*.
  Culture medium: modified LB culture medium (the components of said medium are: 1% trytones, 0.5% yeast extract, 1% sodium chloride, 0.1% glucose, 0.002% TTC, and pH=7.2 to 7.4).

1.3 Experimental Method:
  The *Proteus Mirabilis* were inoculated at the center of an LB plate, incubating at 37° C. for 9 hours, then concentric rings emerged, which were extended outward continually with an interval of 3 hours, and this was taken as a control; adding the compound of formula (I) with a final concentration of 0.5% onto the LB plate, the *Proteus Mirabilis* were inoculated by the same method, cultured at 37° C., and the result showed that not only the concentric rings formed with an interval of 3 hours were emerged, comparing with the control, it can be seen that there were also many fine waves on each ring emerged.

The liquid culture results showed that the compound of formula (I) could promote the growth of lactobacillus.

2. Experimental Results and Evaluation:
  The experiment adopts a bio-wave model which is used to research the promoting wave function of the compound of formula (I). It can be seen from the result that the compound of formula (I) was not only able to cause a bacterial cell to reveal a normal bio-wave characteristic, but also caused the wave to reveal finer wave mode, and these indicated that the compound of formula (I) have a promoting function to bio-waves, and the promoting wave function is able to participate in the repair and redistribution of skin cells.

II. Toxicological Test of the Compound of Formula (I), Including:
1. Acute toxicity test: including tests of oral administration, intravenous injection administration, and maximum limit amount for administration.
2. Ames test;
3. Micronucleus test of mouse bone marrow cell;
4. Abnormality test of mouse sperm;
5. Aberration test of mouse testis chromosome;
6. Chronic lethal test;
7. Subchronic toxicity (feed for 90 days) test;
8. Traditional deformity-inducing test.

The results from these tests showed that in the acute toxicity test of the compound of formula (I), the dosage of more than 2 g/kg was taken, which was 300 times the injection dosage for human beings, but the acute toxicosis reaction had not appeared yet; in the long-period toxicity test, the maximum dosage had reached up to 1 g/kg, and after the treatment and observation for four weeks, there was no intoxication reaction yet; and in the reproduction test, the mouse was fed from a routine dosage of 7 mg/kg for 3 generations, it had been proved that the compound of formula (I) had no influence on the pregnancy, birth, nurse and the growth of the baby mouse, so that the compound of formula (I) is a substance without toxicity.

III. Tests of Effect for Suppressing Bacterial Transplantation
1. Test of effect for suppressing *bacillus pyocyaneus* transplantation on skin
2. Test of suppressing bacteria The results of these two tests indicated that the compound of formula (I) essentially exhibited no bactericidal or bacteriostasis effect, but it suppressed the transplantation and growth of *bacillus* pyocyaneus so as to achieve the object of anti-infection.

IV. Clinic Tests
1. 170 patients suffering various venereal diseases were picked out, including 50 patients suffering gonorrhea, 50 patients suffering syphilis, 20 patients suffering condyloma acuminatum virus infection, 40 patients suffering trichomonas vaginalis infection, and 10 patients suffering *candida albicans*. 2% N-acetyl-D-glucosamine aerosol was topically sprayed to infected areas, and the effects of the compound of formula (I) for treatment of urogenital tract infections were determined by smearing and microscopic examination, and by isolation and culture. The results showed that the effective rate of N-acetyl-D-glucosamine for treatment of various urogenital tract infections is 79% as depicted in the following table.

Observation of therapeutical effect of N-acetyl-D-glucosamine for treatment of urogenital tract infections

| Infection pathogen | Case number | Effective rate (%) | Ineffective rate (%) |
| --- | --- | --- | --- |
| Gonorrhea | 50 | 90 | 10 |
| Syphilis | 50 | 60 | 40 |
| condyloma acuminatum virus infection | 20 | 80 | 20 |
| *trichomonas vaginalis* infection | 40 | 75 | 25 |
| *candida albicans* | 10 | 90 | 10 |

INDUSTRIAL APPLICABILITY

The present invention pioneers a novel medial use of N-acetyl-D-glucosamine, extends the application range of N-acetyl-D-glucosamine, and increases the use value of N-acetyl-D-glucosamine. The external formulations in various forms prepared with N-acetyl-D-glucosamine as active components are used as a medicament for prevention and treatment of urogenital tract infections, and exhibit advantages of easy preparation and no toxic and side effect. Since it is a colorless, insipid and nonirritant substance, and has a novel action route, its use exhibits unique therapeutic effect and avoids disadvantages of other products.

What is claimed is:

1. A method for treating a subject suffering from urogenital tract infection, the method comprising administering to the subject an effective amount of a medicament containing N-acetyl-D-glucosamine and/or pharmaceutical acceptable salts thereof.

2. The method according to claim 1, wherein said medicament is a formulation in the form for topical administration.

3. The method according to claim 2, wherein said medicament is a formulation in a form selected from a group consisting of lotion, aqua, emulsion, cream, ointment, and suppository.

4. The method according to claim 1, wherein a daily dose of the administration is 100 to 2000 mg of N-acetyl-D-glucosamine.

5. The method according to claim 1, wherein a concentration of N-acetyl-D-glucosamine in said medicament is 0.1 to 10% by weight.

6. The method according to claim 2, wherein a daily dose of the administration is 100 to 2000 mg of N-acetyl-D-glucosamine.

7. The method according to claim 3, wherein a daily dose of the administration is 100 to 2000 mg of N-acetyl-D-glucosamine.

8. The method according to claim 2, wherein a concentration of N-acetyl-D-glucosamine in said medicament is 0.1 to 10% by weight.

9. The method according to claim 3, wherein a concentration of N-acetyl-D-glucosamine in said medicament is 0.1 to 10% by weight.

10. A method for treating a subject suffering from urogenital tract infection, the method comprising administering to the subject an effective amount of a medicament containing as the only active ingredient N-acetyl-D-glucosamine and/or pharmaceutically acceptable salts thereof.

11. The method according to claim 10, wherein said medicament is a formulation in the form for topical administration.

12. The method according to claim 11, wherein said medicament is a formulation in a form selected from a group consisting of lotion, aqua, emulsion, cream, ointment, and suppository.

13. The method according to claim 10, wherein a daily dose of the administration is 100 to 2000 mg of N-acetyl-D-glucosamine.

14. The method according to claim 10, wherein a concentration of N-acetyl-D-glucosamine in said medicament is 0.1 to 10% by weight.

15. The method according to claim 11, wherein a daily dose of the administration is 100 to 2000 mg of N-acetyl-D-glucosamine.

16. The method according to claim 12, wherein a daily dose of the administration is 100 to 2000 mg of N-acetyl-D-glucosamine.

17. The method according to claim 11, wherein a concentration of N-acetyl-D-glucosamine in said medicament is 0.1 to 10% by weight.

18. The method according to claim 12, wherein a concentration of N-acetyl-D-glucosamine in said medicament is 0.1 to 10% by weight.

* * * * *

UNITED STATES PATENT AND TRADEMARK OFFICE
CERTIFICATE OF CORRECTION

PATENT NO. : 7,704,976 B2
APPLICATION NO. : 10/524476
DATED : April 27, 2010
INVENTOR(S) : Qiwang Xu et al.

It is certified that error appears in the above-identified patent and that said Letters Patent is hereby corrected as shown below:

*Col. 1, line 30, "inventor has" should be -- inventors have --.

*Col. 1, lines 36 and 45, "kind" should be -- kinds --.

•Col. 1, line 54, "(WO18702244)" should be -- (WO/8702244) --.

*Col. 2, line 6, "pharmaceutical" should be -- pharmaceutically --.

*Col. 2, line 12, "pharmaceutical" should be -- pharmaceutically --.

*Col. 2, lines 37 and 39, "pharmaceutical" should be -- pharmaceutically --.

Col. 2, line 47, "(I)" should be -- (1) --.

Col. 3, lines 4 and 5, "inventor deems ... formula (I)" should be -- inventors deem ... formula (1) --.

Col. 3, line 32, "1." should be -- I. --.

Col. 3, line 48, "(I)" should be -- (1) --.

*Col. 3, line 53, After "that" delete "there were also".

*Col. 3, line 65, "have" should be -- has --.

*Col. 4, line 66, "medial" should be -- medical --.

*Col. 5, claim 1, line 14, "pharmaceutical" should be -- pharmaceutically --.

Signed and Sealed this

Ninth Day of November, 2010

David J. Kappos
*Director of the United States Patent and Trademark Office*